(12) United States Patent
Orr et al.

(10) Patent No.: US 10,786,645 B2
(45) Date of Patent: Sep. 29, 2020

(54) CAPNOMETRY SYSTEM WITH SUPPLEMENTAL OXYGEN DETECTION AND METHOD OF OPERATION THEREOF

(71) Applicant: KONINKLIJKE PHILIPS N.V., Eindhoven (NL)

(72) Inventors: Joseph Allen Orr, Park City, UT (US); Lara Marie Brewer, Bountiful, UT (US)

(73) Assignee: Koninklijke Philips N.V., Eindhoven (NL)

( * ) Notice: Subject to any disclaimer, the term of this patent is extended or adjusted under 35 U.S.C. 154(b) by 432 days.

(21) Appl. No.: 15/540,137

(22) PCT Filed: Dec. 17, 2015

(86) PCT No.: PCT/IB2015/059708
§ 371 (c)(1),
(2) Date: Jun. 27, 2017

(87) PCT Pub. No.: WO2016/108127
PCT Pub. Date: Jul. 7, 2016

(65) Prior Publication Data
US 2017/0368294 A1 Dec. 28, 2017

Related U.S. Application Data

(60) Provisional application No. 62/097,946, filed on Dec. 30, 2014.

(51) Int. Cl.
*A61M 16/10* (2006.01)
*A61M 16/00* (2006.01)
(Continued)

(52) U.S. Cl.
CPC ....... *A61M 16/1005* (2014.02); *A61B 5/0803* (2013.01); *A61B 5/0836* (2013.01);
(Continued)

(58) Field of Classification Search
CPC ..... A61B 5/097; A61B 5/0836; A61B 5/0803; A61B 5/746; A61M 16/085;
(Continued)

(56) References Cited

U.S. PATENT DOCUMENTS 5,165,397 A 11/1992 Arp
6,668,824 B1 * 12/2003 Isaza ................ A61M 16/0051
128/202.22
(Continued)

FOREIGN PATENT DOCUMENTS

WO    WO-2013054217 A1 *  4/2013  ........ A61M 16/0051

*Primary Examiner* — Timothy A Stanis
*Assistant Examiner* — Thao Tran
(74) *Attorney, Agent, or Firm* — Daniel H. Brean

(57) ABSTRACT

A capnography system (100, 400), comprising: a controller (110, 410) configured to obtain a sample gas flow from a physical interface (107) for a patient (101); determine a change in a characteristic of the sample gas flow during a sampling time interval; determine whether the change in the characteristic of the sample gas flow during the sampling time interval is equal to or greater than a corresponding threshold value; determine that supplemental oxygen is provided when it is determined that the change in the characteristic of the sample gas flow is equal to or greater than the threshold value; and determine that supplemental oxygen is not provided when it is determined that the change in the characteristic of the sample gas flow is less than the threshold value.

12 Claims, 5 Drawing Sheets

(51) Int. Cl.
*A61M 16/08* (2006.01)
*A61B 5/083* (2006.01)
*A61B 5/08* (2006.01)
*A61B 5/00* (2006.01)
*A61M 16/12* (2006.01)

(52) U.S. Cl.
CPC ......... *A61B 5/746* (2013.01); *A61M 16/0051* (2013.01); *A61M 16/024* (2017.08); *A61M 16/085* (2014.02); *A61B 5/742* (2013.01); *A61B 2560/0266* (2013.01); *A61M 16/0808* (2013.01); *A61M 16/12* (2013.01); *A61M 2016/003* (2013.01); *A61M 2016/0027* (2013.01); *A61M 2016/103* (2013.01); *A61M 2016/1025* (2013.01); *A61M 2016/1035* (2013.01); *A61M 2202/0208* (2013.01); *A61M 2202/0225* (2013.01); *A61M 2202/0266* (2013.01); *A61M 2205/18* (2013.01); *A61M 2205/3303* (2013.01); *A61M 2205/3306* (2013.01); *A61M 2205/3331* (2013.01); *A61M 2205/3334* (2013.01); *A61M 2205/3368* (2013.01); *A61M 2205/3553* (2013.01); *A61M 2205/3561* (2013.01); *A61M 2205/3584* (2013.01); *A61M 2205/505* (2013.01); *A61M 2205/52* (2013.01); *A61M 2230/432* (2013.01); *A61M 2230/435* (2013.01); *A61M 2230/437* (2013.01)

(58) Field of Classification Search
CPC .......... A61M 16/0858; A61M 2230/43; A61M 2230/432; A61M 16/1005; A61M 16/024; A61M 16/0051; A61M 2205/3303; A61M 2205/3334; A61M 2205/52; A61M 2205/505; A61M 2016/003; A61M 2016/0027; A61M 16/0003; A61M 16/0015

See application file for complete search history.

(56) References Cited

U.S. PATENT DOCUMENTS

| | | | |
|---|---|---|---|
| 7,305,988 B2 | 12/2007 | Acker et al. | |
| 7,684,931 B2 | 3/2010 | Pierry et al. | |
| 8,161,972 B2* | 4/2012 | Isaza | A61M 16/0468 128/207.16 |
| 8,322,339 B2* | 12/2012 | Gottlib | A61M 16/0051 128/205.23 |
| 8,992,430 B2 | 3/2015 | Colman et al. | |
| 2002/0112726 A1* | 8/2002 | Schmidt | A61M 16/026 128/204.23 |
| 2005/0115561 A1* | 6/2005 | Stahmann | A61B 5/0031 128/200.24 |
| 2006/0086357 A1* | 4/2006 | Soliman | A61M 16/0051 128/204.22 |
| 2009/0118633 A1 | 5/2009 | Jaffe et al. | |
| 2010/0078024 A1 | 4/2010 | Andrieux et al. | |
| 2014/0007878 A1 | 1/2014 | Armitstead et al. | |
| 2014/0076317 A1 | 3/2014 | Lotz et al. | |
| 2014/0216451 A1* | 8/2014 | Jaffe | A61M 16/0051 128/202.22 |
| 2014/0301949 A1 | 10/2014 | Rabi | |
| 2015/0273172 A1 | 10/2015 | Pessala et al. | |

\* cited by examiner

CAPNOMETRY SYSTEM WITH SUPPLEMENTAL OXYGEN DETECTION AND METHOD OF OPERATION THEREOF

This application is a national stage application under 35 U.S.C. § 371 of International Application No. PCT/IB2015/059708 filed on Dec. 17, 2015 and published in the English language on Jul. 7, 2016 as International Publication No. WO2016/108127, which claims priority to U.S. Patent Application No. 62/097,946 filed on Dec. 30, 2014, the entire disclosures of which are incorporated herein by reference.

The present system relates to a capnography system for detecting the presence or absence of oxygen in a ventilation gas obtained from a physical user interface, such as a system for detecting the presence of oxygen in a side-steam flow of a ventilation stream configured to be coupled to a spontaneously breathing patient, and a method of operation thereof.

Typically, nasal capnometry can be used to detect periods of slow and/or inadequate breathing in patients who may be at risk of inadequate ventilation such as patients who are on certain medications. For example, analgesic and/or sedative medications can temporarily reduce a patient's desire and ability to breathe which may cause the patient to be ventilated inadequately. Some level of decreased breathing may be acceptable for a short period of time when supplemental oxygen is administered through a nasal cannula or an oxygen mask. Unfortunately, clinicians may often forget to administer supplemental oxygen to a patient when it would be beneficial. Alternatively, clinicians may provide or continue to provide supplemental oxygen when it is not necessary or undesirable (e.g. the addition of supplemental oxygen may increase the inaccuracy of measured capnogram making it difficult or impossible to accurately analyze the capnogram or information related thereto). Accordingly, embodiments of the present system may overcome these and/or other disadvantages in prior systems.

The system(s), device(s), method(s), arrangements(s), user interface(s), computer program(s), processes, etc. (hereinafter each of which will be referred to as system, unless the context indicates otherwise), described herein may address problems in prior systems.

In accordance with embodiments of the present system, there is disclosed a capnography system including a controller configured to obtain a sample gas flow from a physical interface for a patient; determine at least one of concentration and partial pressure of carbon dioxide in the sample gas flow during a sampling time interval; determine whether a change in pressure in the sample gas flow during the sampling time interval is equal to or greater than a threshold value; determine that supplemental oxygen is provided when it is determined that the change in pressure is equal to or greater than the threshold value; and determine that supplemental oxygen is not provided when it is determined that the change in pressure is less than the threshold value. The controller may be configured to form a message which indicates whether supplemental oxygen is determined to be provided. The controller may be configured to form a first message which indicates that supplemental oxygen is recommended when it is determined that supplemental oxygen is not provided and one or more patient conditions indicates that supplemental oxygen is recommended. The controller may be configured to form a second message which indicates that supplemental oxygen is not recommended when it is determined that supplemental oxygen is provided and the one or more patient conditions indicates that supplemental oxygen is not recommended. The controller may be configured to render a third message that is an alarm message when the controller renders at least one of the first and second messages.

A rendering portion may be coupled to the controller. The controller may be configured to render the message using the rendering portion. A flow restrictor may be fluidically coupled to the physical interface. The controller may be configured to obtain the sample gas flow through the flow restrictor and determine the change in pressure as a change in differential pressure in the sample gas flow. The controller may be configured to determine the change in pressure as a ratio of change in differential pressure to change in sample pressure. The controller may be configured to render the determined at least one of concentration and partial pressure of carbon dioxide gas.

In accordance with embodiments of the present system, there is disclosed a capnography system including a controller which obtains a sample gas flow from a physical interface coupled to a user; determines at least one of concentration and partial pressure of carbon dioxide in the sample gas flow during a sampling time interval; determines whether a change in pressure in the sample gas flow during the sampling time interval indicates that supplemental oxygen is being provided; and renders results of the determination. The controller may determine that the supplemental oxygen is not provided when it is determined that the change in pressure is less than a threshold pressure value. A pneumatic system may provide a ventilation gas to the physical interface for inhalation by the user. The system may include a rendering device wherein the controller renders a graph of concentration of at least one of carbon dioxide and oxygen gasses.

In accordance with embodiments of the present system, there is disclosed a method of determining whether supplemental oxygen is being provided in a capnographic system. The method may include acts of obtaining a sample gas flow from a physical interface for a patient; determining at least one of concentration and partial pressure of carbon dioxide in the sample gas flow during a sampling time interval; determining whether a change in pressure in the sample gas flow during the sampling time interval is equal to or greater than a threshold value; determining that supplemental oxygen is provided when it is determined that the change in pressure and or sampling gas flow is equal to or greater than the threshold value(s); and determining that supplemental oxygen is not provided when it is determined that the change in pressure and or sampling gas flow is less than the threshold value. The method may include an act of forming a message which indicates whether supplemental oxygen is determined to be provided.

In accordance with embodiments of the present system, the method may include acts of determining whether one or more patient conditions indicates that supplemental oxygen is recommended; forming a first message which indicates that supplemental oxygen is recommended when it is determined that supplemental oxygen is not provided and the one or more patient conditions indicates that supplemental oxygen is recommended; and forming a second message which indicates that supplemental oxygen is not recommended when it is determined that supplemental oxygen is provided and the one or more patient conditions indicates that supplemental oxygen is not recommended. The method may include an act of rendering a third message that is an alarm message when the controller renders at least one of the first and second messages. The method may include an act of determining the change in pressure as a change in differential pressure in the sample gas flow. The method may include an act of determining the change in pressure as a ratio of change in differential pressure to change in sample pressure.

The present invention is explained in further detail in the following exemplary embodiments and with reference to the figures, where identical or similar elements may be partly indicated by the same or similar reference numerals, and the features of various exemplary embodiments being combinable. In the drawings.

The following are descriptions of illustrative embodiments that when taken in conjunction with the following drawings will demonstrate one or more of the above noted features and advantages, and/or further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

Figure 1:
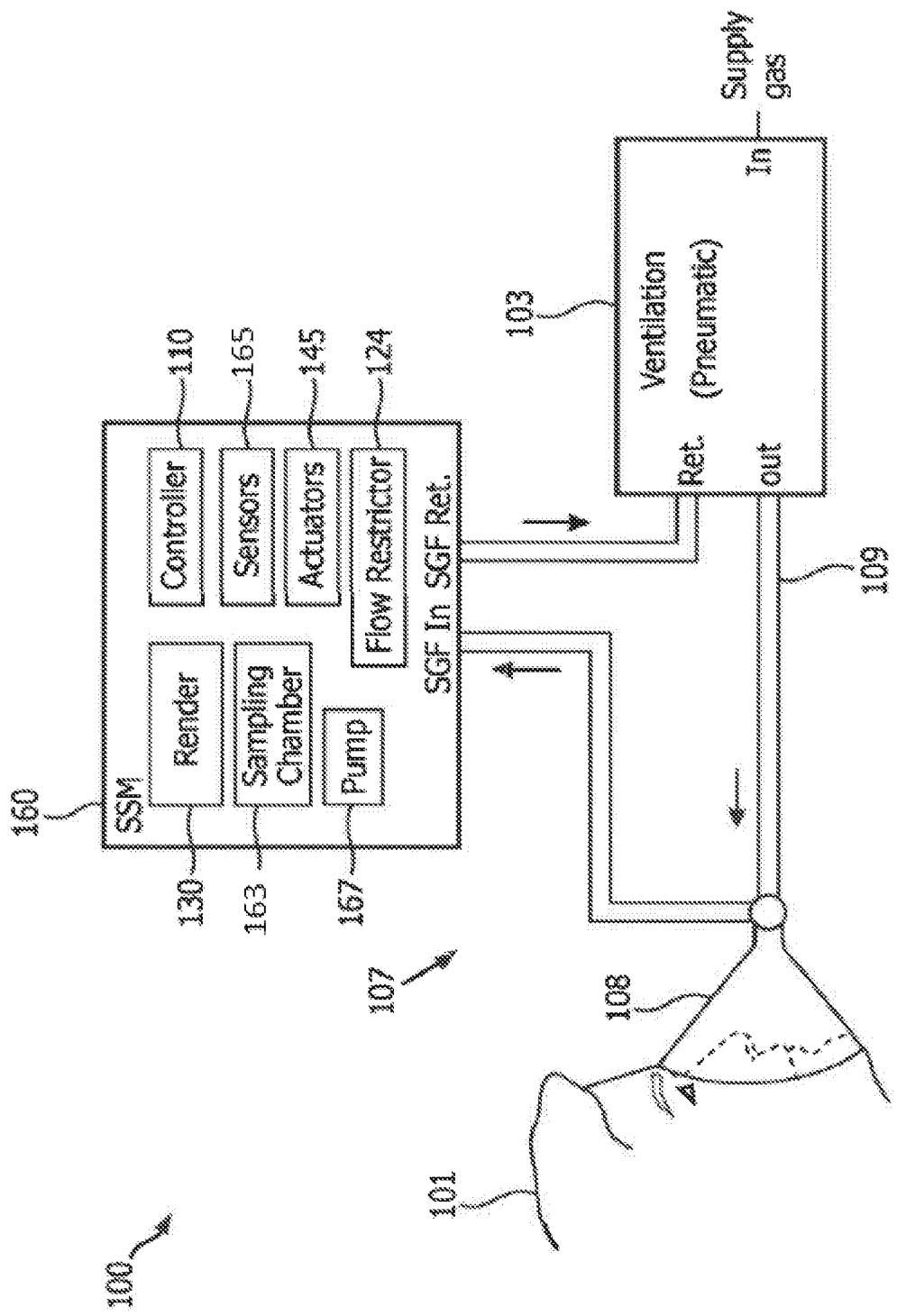
FIG. 1 shows a block diagram of a capnometry system operating in accordance with embodiments of the present system.

FIG. 1 shows a block diagram of a capnometry system 100 (hereinafter system 100 for the sake of clarity) operating in accordance with embodiments of the present system. The system 100 may include a side-steam monitor (SSM) 160 which may be coupled to a ventilation portion 103 using any suitable method so as to receive a sample gas flow (SGF) at an input (SGF IN). The SSM 160 may then analyze at least a portion (e.g., a sample portion) of the SGF using one or more sensors 164, and output the SGF at an output (SGF RET). The output SGF may then be provided to a desired portion such as the ventilation portion 103 or vented to atmosphere, if desired.

In accordance with embodiments of the present system, the capnometry system 100 may be used for spontaneously breathing patients such as those receiving supplemental oxygen by nasal cannula or face mask. In accordance with embodiments of the present system, the capnometry system 100 may also be utilized with a patient utilizing a ventilator, however, as may be readily appreciated, the O2 status for a ventilated patient is not as questionable as it is during spontaneous breathing.

The ventilation portion 103 may provide a gas for ventilation (hereinafter ventilation gas) of a patient 101. Accordingly, the ventilation portion may receive one or more gasses (e.g., $O_2$, nitrogen ($N_2$), air, water vapor, etc.) at an input end (IN), mix these gasses to form the ventilation gas, and output the ventilation gas at an output (OUT). Accordingly, the ventilation gas may, depending upon system settings and/or time, include a single gas (e.g., $O_2$) or a gas mixture such as an $N_2$ and $O_2$ gas mixture, etc. The ventilation portion 103 may be coupled to a patient 101 using any suitable coupling such as a ventilation coupler 107 which may include one or more hoses 109 (e.g., tubing) and/or a patient interface 108. The patient interface 108 may be of any suitable type of system interface (e.g., a user interface, UI) such as a non-invasive (e.g., a mask as shown, a nasal adapter, a nasal cannula, etc.) types so as to provide the ventilation gas to the patient 101 for inspiration. The patient interface 108 may include a holding portion such as tabs, straps, etc., which may hold the patient interface 108 in position relative to the patient 101 during use, if desired. In use, the ventilation coupler 107 may further receive exhaled gasses (e.g., expiration gasses) from the patient 101 such as gasses from within the respiratory tract of the patient. Accordingly, the SGF may, at certain times, include at least some of these exhaled gasses as may be described elsewhere. The ventilation portion 103 may include one or more pumps to pressurize an input gas such as air, and/or to provide a desired flow rate, pressure, etc. of the ventilation gas.

In accordance with some embodiments, the ventilation coupler 107 may include one or more passive or active valves such as passive one-way valves which may direct the flow of gasses within the ventilation coupler in a desired direction or directions. For example, the ventilation gas may be provided to the patient 101 for inspiration and expiration gases from the patient 101 may be directed in a different direction. In accordance with some embodiments, the ventilation coupler 107 may further include conditioners such as dryers which may, for example, remove moisture from the SGF and/or trap condensation, if desired. Further, in accordance with yet other embodiments, the ventilation portion 103 may include pumps, valves, and/or mixers operating under the control of the controller 110 to mix water vapor, and/or medication into the ventilation gas, if desired. The ventilation portion 103 may include a return port to receive a return gas for further processing, if desired. Thereafter, this return gas, or portions thereof, may be mixed with the ventilation gas to be output to the ventilation coupler 107 for reuse, as desired.

Referring back to the SSM 160, this portion may include one or more of sensors 164, a controller 110, actuators 165, a pump 167, a sampling chamber 163, and a rendering portion 130. In accordance with embodiments of the present system, the controller 110 may control the overall operation of the SSM 160. The actuators 165 may include one or more motors, transducers, etc. which may provide a force to operate one or more valves, mixers, or the like of the SSM 160 for example under the control of the controller 110. The sampling chamber 163 may include one or more sampling chambers in which a sample portion of the SGF may be analyzed by the sensors 164. The pump 167 may be operative under the control of the controller 110 to control a flow of the SGF as may be described elsewhere.

The sensors 164 may include at least one sensor which may analyze at least a portion of the SGF within the sampling chamber 163. Further, the sensors 164 may include temperature, volume, concentration, and/or pressure sensors to detect temperature, volume, concentration, and/or pressure, respectively, of the SGF within the sampling chamber 163 in accordance with embodiments of the present system. In accordance with some embodiments, sensors 164 may include electro-optic sensors which may analyze the SGF and determine characteristics of one or more gasses within the SGF such as the presence, temperature, concentration, volume and/or pressure of one or more gasses within the SGF which may be located within the sampling chamber 163. The sensors 164 may then form corresponding sensor information and provide this information to the controller 110 for further processing.

In accordance with embodiments of the present system, the controller 110 may then render the results of the analysis using any suitable rendering device 130 such as a display. The rendering device may be locally and/or remotely located and may communicate with the controller 110 via any suitable bus or network such as the Internet, etc. In accordance with embodiments of the present system, the sensors 164 may be tuned or otherwise configured to detect presence and/or characteristic of a desired gas (e.g., $CO_2$, $O_2$, $N_2$, etc.). Accordingly, the sensors 164 may detect one or more corresponding gasses within the SGF such as carbon dioxide ($CO_2$), oxygen ($O_2$), nitrogen ($N_2$), etc., and may form corresponding sensor information. For purposes of simplifying the description of embodiments of the present system, the system will be described with regard to detection of only characteristics of carbon dioxide (CO2) in the SGF by the sensors 164. For example, in accordance with embodiments of the present system, the sensors 164 may analyze the SGF and detect/determine one or more characteristics of one or more gasses, such as at a concentration and/or a partial pressure of $CO_2$ within the SGF located within the sampling chamber 163. However, as may be readily appreciated, characteristics of other gases and/or combinations thereof in the SGF may be sensed by the sensors 164 in accordance with embodiments of the present system.

The controller 110 may then analyze the sensor information to determine characteristics of the sensed gas over time. Once characteristics of the one or more sensed gas are determined such as concentration, etc., the controller 110 may then control the renderer 130 to render results of the determination.

Referring back to the ventilation portion 103, in accordance with embodiments of the present system, this portion may be controlled by a ventilation controller, the controller 110 and/or other controller so as to provide the ventilation gas for ventilating the patient 101 at a desired volume, flow, pressure, and/or mixture.

Figure 2:
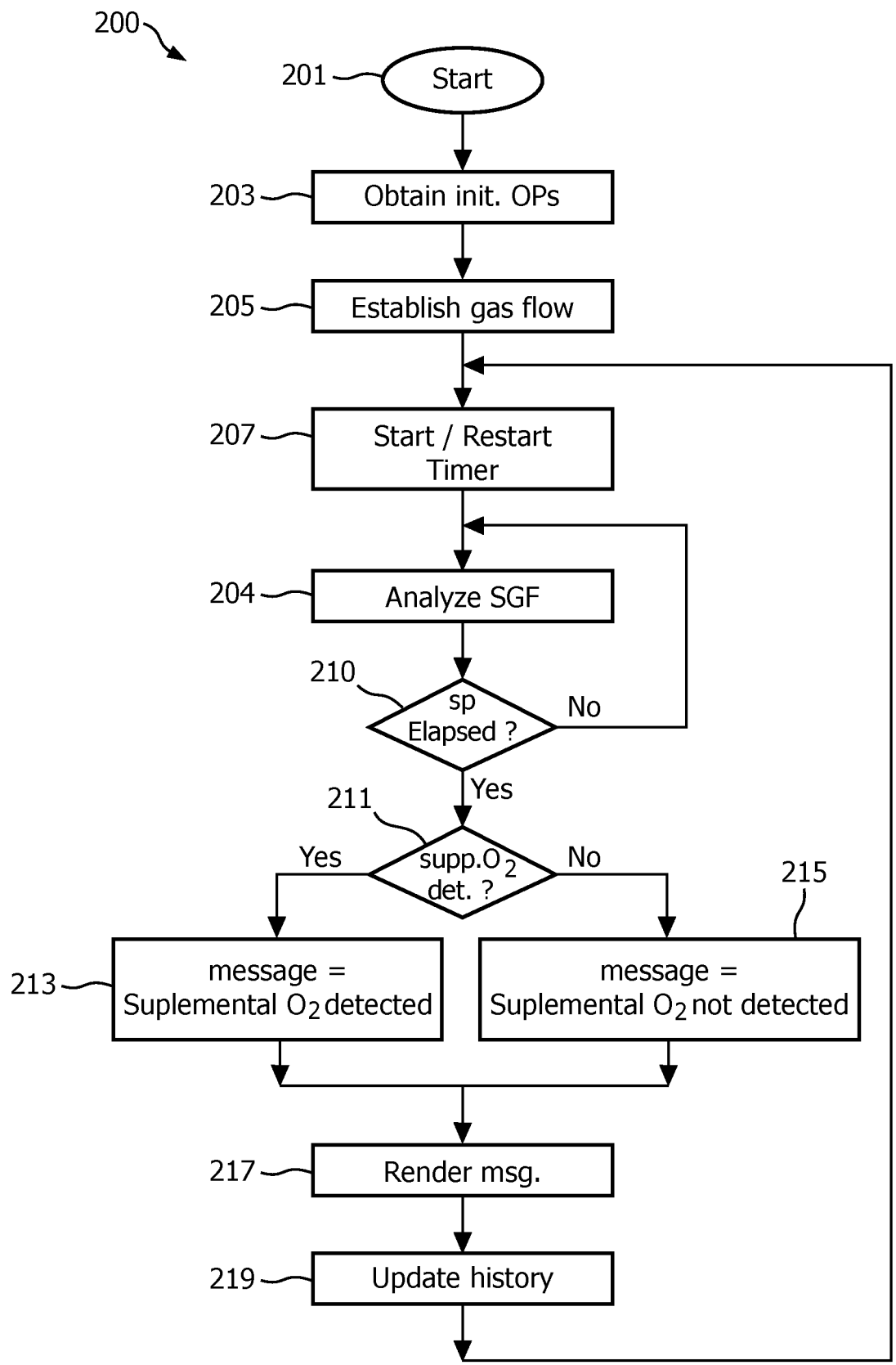
FIG. 2 shows a functional flow diagram performed by a guidance process in accordance with embodiments of the present system.

FIG. 2 shows a functional flow diagram performed by a process 200 in accordance with embodiments of the present system. The process 200 may be performed using one or more computers communicating over a network and may obtain information from, and/or store information to one or more memories which may be local and/or remote from each other. The process 200 may include one of more of the following acts. In some embodiments, the acts of process 200 may be performed using one or more suitable gas monitoring system(s) such as a side-stream monitoring system (SSM) operating in accordance with embodiments of the present system. Further, one or more of these acts may be combined, reordered and/or separated into sub-acts, as desired. Further, one or more of these acts may be skipped depending upon settings. In operation, the process may start during act 201 and then proceed to act 203.

During act 203, the process may obtain initial operating parameters such as one or more sampling values, a sample flow rate (SFR) value, information about a ventilated patient (e.g., the patient to be ventilated), etc. The sampling value may denote a sampling time period as set forth herein. In accordance with embodiments of the present system, the greater the sampling value, the longer the sampling time period may be. In accordance with embodiments of the present system, a larger sampling volume may be accommodated by utilizing additional sensors and/or sensors provided with a larger sampling capacity without extending the sampling period. In either event, the sampling volume and/or other characteristic may be set by the system, a user and/or may be obtained from a memory of the system. Further, the process may obtain a sample flow rate (SFR) value which may be used to initialize a sample gas flow pump of the system. The SFR value may be set by the system, the user and/or may be obtained from a memory or in real time, as desired.

Figure 5:
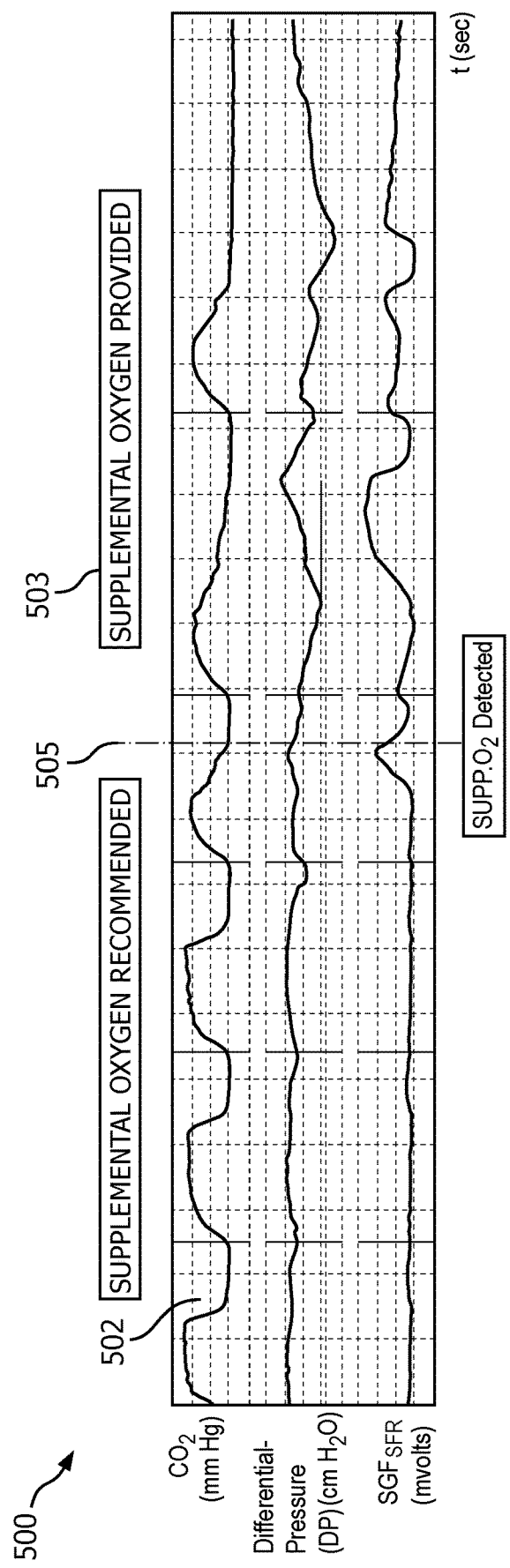
FIG. 5 which shows a graph 500 including a capnogram 502 and the clinical message formed in accordance with embodiments of the present system.

The information about the ventilated patient, such as information about whether or not the ventilated patient has received one or more drugs likely to provide analgesia and/or sedation may be utilized, for example, by the process to determine whether to provide an indication whether or not supplemental oxygen is recommended (e.g., see FIGS. 2, 5, and act 217). In accordance with embodiments of the present system, more or less information about the ventilated patient may be utilized (e.g., for example by an expert system trained in accordance with embodiments of the present system) for determining whether or not to provide an indication that supplemental oxygen is recommended. In accordance with one or more embodiments of the present system, information about the ventilated patient may not be required and/or no recommendation may be provided. After completing act 203, the process may continue to act 205.

During act 205, the process may establish a sample gas flow (SGF) of the system. Accordingly, the process may control an SGF pump to provide the SGF at a desired sample flow rate as may be set by the SFR value. The SGF may be obtained from one or more SGF tubes coupled to a sampling system interface such as a nasal cannula coupled to the patient and which receives a ventilation gas from the ventilation portion. In accordance with embodiments or the present system, the process may wait for a sample period of time to elapse (e.g., 20 sec., etc.), so that at least a portion of the SGF may be provided to one or more sampling chambers of the system. The process may further obtain sensor information to determine, for example, an ambient pressure within one or more of the sampling chambers. The process may further determine a sample flow rate of the SGF in real time. Further, the process may control the SGF pump to maintain a fixed flow of the SGF in real time based upon the feedback information such as flow rate information obtained from one or more flow rate sensors of the system. After completing act 205, the process may continue to act 207. In accordance with embodiments of the present system, it is envisioned that the sample gas pump may be optional.

During act 207, the process may start/restart a timer such as a count-down timer and/or other timer to an initial sampling value. This initial sampling value may set forth a sampling period (SP) (e.g., a sampling time period) during which a sample of gas flow may be acquired. For example, the initial sampling value may be set to a default value (e.g., 10 sec.). In yet other embodiments, the timer may include an up-count timer in which case the process may set and start the timer with a default start value such as 0. The initial sampling value may then correspond with a maximum sampling time as counted by the timer. However, for the sake of simplifying the discussion herein, a count-down timer is discussed with regard to the present system. Further, in accordance with embodiments of the present system, the sampling period may vary based upon one or more variables that may be determined by the process such as accuracy, detected breathing rate, etc. in real time. After completing act 207, the process may continue to act 209.

During act 209, the process may begin to analyze at least a portion of the SGF and may determine whether one or more gasses are present, amounts (e.g., by volume and/or percent) and/or other characteristics of the detected gas and/or gasses over a sampling time period (e.g., as may be set by the initial sampling value). Accordingly, during the sampling time period, the process may detect one or more characteristics of one or more selected gas or gas mixture such as $CO_2$ and $O_2$ in the SGF located in a sampling chamber (e.g., see, FIG. 1, sampling chamber 163), differential pressure (DP) (e.g., differential pressure (cm $H_2O$)), SGF flow rate ($SGF_{SFR}$) (ml/min as may be represented by a voltage signal) as may be determined using corresponding sensors. In accordance with embodiments of the present system, act 209 may be initiated and/or otherwise performed during other times of the process 200, such as coincident with the establishment of the gas flow. This is illustrated with respect to FIG. 3 which shows a graph 300 which illustrates determined values for $CO_2$, differential pressure (DP), and SGF flow rate ($SGF_{SFR}$) for a patient ventilated with and without supplemental oxygen in time in accordance with embodiments of the present system. Generally, N breathing cycles (BCs) are illustrated as BC1 through BCN (generally BCx) and each breathing cycle may include an exhalation phase (EP) and an inhalation phase (IP). For the sake of clarity, it may be assumed that each BC may include a corresponding sampling period time. As illustrated with regard to FIG. 3, initially no supplemental oxygen is applied during BC1 through BC3 and thereafter (e.g., at time $t_{SO}$) supplemental oxygen is applied to the patient. As shown, there may be a slight delay until a steady state is achieved for the supplemental oxygen application state.

The process may then continue during act 210 where it may be determined whether or not the sampling time period has elapsed. In a case wherein it is determined that the sampling time period has not elapsed, the process will continue to analyze the SGF. In a case wherein it is determined that the sampling time period has elapsed, the process will continue to act 211.

It should be noted that in accordance with embodiments of the present system where a threshold is utilized to determine whether or not supplemental oxygen is being provided as discussed herein, the process need not wait for the expiration of the sampling time period. For example, in accordance with embodiments of the present system once it is determined that a threshold condition for example is exceeded, the process may immediately continue with act 213 (i.e., not wait for expiration of the sampling time period) as further described herein. In this way, in accordance with embodiments of the present system, the system may respond (e.g., perform one of acts 213, 215) quicker than in an embodiment wherein a determination is only made after an end to the sampling time period.

In any event and regardless of which of the embodiments of the present system are utilized for detecting the presence of oxygen in the SGF, a determination is made whether or not supplemental oxygen is being provided such as during act 211. The process may use any suitable method to detect supplemental oxygen use as may be described below. However, it is also envisioned that other methods to detect supplemental oxygen use may be suitably applied in accordance with embodiments of the present system.

For example, in accordance with embodiments of the present system, $CO_2$ and/or $O_2$ may be detected based upon an analysis of sensor information from a sensor of a first type such as an infra-red (IR) sensor tuned to detect $CO_2$ over the sampling time period. In accordance with embodiments of the present system, the one or more sensors may provide sensor information to a controller of the system which may analyze the sensor information to detect $CO_2$ and/or $O_2$ and/or to determine for example a presence of supplemental oxygen.

With regard to detecting supplemental oxygen, in accordance with embodiments of the present system, the process may detect characteristics of supplemental oxygen using any suitable method such as a sensor tuned to detect $O_2$. However, in accordance with embodiments of the present system, the presence of supplemental oxygen administered to the patient may be detected based upon an analysis of sensor information from one or more sensors such as one or more pressure sensors (hereinafter pressure sensor for the sake of clarity) which may detect pressure in the sampling chamber.

Further, the $CO_2$ sensor may utilize a non-dispersive infrared (NDIR) technology tuned to detect $CO_2$. In accordance with embodiments of the present system, the sample may be pulled into sampling chamber with a negative pressure generated by a sampling pump such as the pump 167. The internal flow sensor may be utilized to provide information to the controller to maintain a sampling flow rate within a desired range such as 50 mL/min±0.5 mL/min. However, other ranges and/or values are also envisioned in accordance with embodiments of the present system. Accordingly, the controller may for example control one or more pumps such as the pump 167 to maintain the desired sample flow rate. A pressure sensor such as one or more of the sensors 164 may measure the pressure drop near the sampling chamber of the sidestream gas sensor to determine whether supplemental oxygen is in use.

In accordance with embodiments of the present system, the presence of oxygen may be detected for example by evaluating a change in the SGF as it is measured for example using a differential pressure sensor that measures the pressure difference induced by the gas flow as it flows through a small diameter orifice or tube such as a flow restrictor 124 (see, FIG. 1). For example, as the sample gas flows through the flow restrictor, it may create a differential pressure that is proportional to the gas flow rate and the physical characteristics of the gas such as its viscosity and density. In accordance with embodiments of the present system, one or more sensors may be provided to detect a flow rate (e.g., $SGF_{SFR}$), such as a higher or lower flow rate, as the viscosity and/or density of the sampled gas changes. For example, as oxygen has a higher viscosity than air, one or more sensors may be utilized to detect a differential pressure increase as the concentration of oxygen increases during the observation period. In accordance with embodiments of the present system, a flow restrictor may be positioned upstream of the sampling chamber. For example, the flow restrictor may be a restrictor valve positioned in the tubing prior to (e.g., upstream of) the sampling chamber or may simply be provided by a portion of tubing that has a smaller diameter than surrounding tubing.

During normal breathing there is a period at the end of each expiration when breathing pauses and the patient is not drawing gas into or out of the lungs. During this period, for a patient receiving supplemental oxygen, the supplemental oxygen continues to flow near the location (nares or mask) from where the sample is acquired (e.g., drawn by the pump 167). During the pause in breathing, the gas sample may draw in gas containing 100% oxygen, such as when the ventilation gas being provided is 100% oxygen. In accordance with embodiments of the present system, as 100% oxygen has a higher viscosity than either inhaled or exhaled gas, the change in viscosity which causes a brief change in the SGF may be observed during the sampling time for example using a differential pressure type SGF sensor during the pause period when oxygen is in use. In this way, the present system may determine for example by comparison to a threshold change (e.g., a change of more than 50%), whether the change in the SGF indicates that supplemental oxygen is in use and thereby, provide an indication of such use or non-use. When supplemental oxygen is not in use, no such peak (e.g., a change of more than 50%) and/or subsequent valley is detected in the measured SGF signal thereby indicating that supplemental oxygen is not in use.

Figure 3:
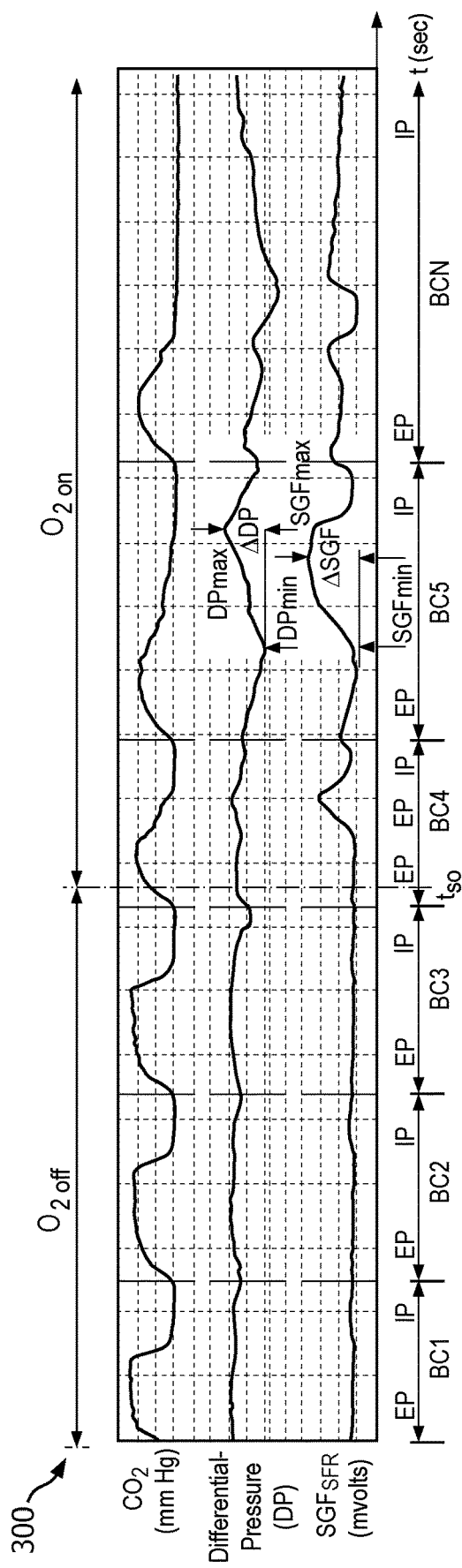
FIG. 3 shows a graph which illustrates determined values for $CO_2$, differential pressure (DP), and SGF flow rate ($SGF_{SFR}$) for a patient ventilated with and without supplemental oxygen in time in accordance with embodiments of the present system.

For example, these peaks are illustratively shown in FIG. 3 during each of BC4 through BCN of graph 300. In accordance with embodiments of the present system, these peaks may be detected during a corresponding breathing phase (e.g., an exhalation phase) of a breathing cycle (e.g., during a corresponding sampling time period). For example, a suitable peak detection method may be used to detect peaks of a differential pressure signal (DP) which are greater than a threshold peak value. When these peaks are detected, the process may determine that supplemental oxygen is being applied (e.g., provided). Conversely, in a case wherein these peaks are not detected (e.g., as shown during BC1 through BC3), the process may determine that supplemental oxygen is not being applied. For example, in accordance with embodiments of the present system, the process may determine whether supplemental oxygen is being applied by determining whether the sample chamber pressure during a breath varies by more than a corresponding threshold value (e.g., a differential pressure threshold value ($DP_{thresh}$)). This variation may be represented as $\Delta DP = DP_{max} - DP_{min}$ as shown in FIG. 3. Accordingly, the process may determine whether $\Delta DP$ is greater than or equal to $DP_{thresh}$. In accordance with embodiments of the present system, when it is determined that $\Delta DP$ is greater than or equal to $DP_{thresh}$, the process may determine that supplemental oxygen is being applied. However, n a case when it is determined that $\Delta DP$ is not greater than or equal to (e.g., less than) $DP_{thresh}$, the process may determine that supplemental oxygen is not being applied.

Similarly, in accordance with embodiments of the present system, the process may determine whether supplemental oxygen is being applied by determining whether a change in the $SGF_{SFR}$ ($\Delta SGF$) during a BC varies more than a corresponding threshold value (e.g., $SGF_{thresh}$). This change in the $SGF_{SFR}$ may be represented as ($\Delta SGF$) and is illustratively shown in FIG. 3 for one BC where $\Delta SGF = SGF_{max} - SGF_{min}$. Accordingly, the process may determine whether $\Delta SGF$ is greater than or equal to $SGF_{thresh}$. In a case when it is determined that $\Delta SGF$ is greater than or equal to $SGF_{thresh}$, the process may determine that supplemental oxygen is being applied. However, in a case when it is determined that $\Delta SGF$ is not greater than or equal to (e.g., less than) $SGF_{thresh}$, the process may determine that supplemental oxygen is not being applied. In accordance with embodiments of the present system $SGF_{thresh}$ may be set (e.g., such as by a default value and/or other desired value, such as set by a user), so that it may correspond with a value, such as a change of 1 ml/min. In accordance with embodiments of the present system, a value may be determined/set, for example, that is more than twice as large as a change in the SGF observed during periods other than the expiratory pause. Accordingly, the process may set the value of $SGF_{thresh}$ in accordance with value of the SGF observed during periods other than an expiratory pause (e.g., to twice this value) or to a predetermined value (e.g., a value equal to 1 ml/min SGF as discussed above). In accordance with embodiments of the present system, the process may analyze the SGF to determine changes in the SGF during a breath. Further, after the changes are detected, the process may act to control the flow range of the SGF so that it may substantially operate within a desired range, such as a range of about 49.5 to 50.5 ml/min. Accordingly, in accordance with embodiments of the present system, when the SGF changes by more than 1 ml/min during a breath, the process may determine that supplemental oxygen is being applied.

In accordance with some embodiments, the process may determine that supplemental oxygen is applied based upon a comparison of a ratio of the change in the SGF to the change in the DP. For example, in accordance with embodiments of the present system, this ratio may be represented as $R_{SFDP} = \Delta SGF / \Delta DP$. Accordingly, in these embodiments when it is determined that $R_{SFDP}$ is greater than or equal to one, the process may determine that supplemental oxygen is being applied. However, when it is determined that $R_{SFDP}$ is not greater than or equal to one, the process may determine that supplemental oxygen is not being applied.

The value of corresponding thresholds (e.g., DPthresh, SGFthresh, etc.) may be set in accordance with system (e.g., a default value) and/or user settings and may be varied to increase or decrease sensitivity of the determinations of the process. Further, the values of thresholds may be stored in a memory of the system for later use, as desired.

Thus, in accordance with embodiments of the present system, a change in observed $SGF_{SFR}$ and/or DP may be detected to determine whether supplemental oxygen is being applied. Accordingly, when it is determined that a change in DP for example beyond a threshold level at the sampling point (e.g., in the mask or cannula) is detected, the process may determine that supplemental oxygen is being applied. In these embodiments, when the change in the SGF is large such as more than twice as large as the change observed during periods other than the expiratory pause or for example more than 1 ml/min change during the interval of a breath, the process may determine that supplemental oxygen is being applied. The SGF system may actively control the flow of the SGF to stay and/or attempt to maintain it within a controlled flow range (i.e. 49.5 ml/min<flow<50.5 ml/min). In accordance with embodiments of the present system, when the SGF changes by more than this during a breath then in accordance with embodiments, the present system may conclude that supplemental oxygen is being provided. Sample chamber pressure change (e.g., as may be represented as $\Delta DP$) during a breath ($DP_{max} - DP_{min}$) may normally be expected to vary by less than 1 cm H2O for example when no supplemental oxygen is being applied. Changes larger than this for a patient that is not intubated (does not have a breathing tube in place) may be utilized in accordance with embodiments as an indication that supplemental oxygen is in use. As a percent the $SGF_{SFR}$ generally changes more than does the sample pressure (DP), a ratio of the max-min difference in $SGF_{SFR}$ (in ml/min) during a breath to the max-min difference in sample chamber pressure (in cm $H_2O$) of greater than 1.0 may be utilized as an indication that supplemental oxygen is in use.

In accordance with embodiments of the present system, the pressure sensor may detect pressure (DP) within the sampling chamber and/or area over the sampling time period and/or portions of the sampling time period (e.g., such as at a time of exhalation and/or following inhalation) and provide this information to the controller for further processing in accordance with embodiments of the present system. In this way, the process may determine whether or not supplemental oxygen is being provided, such as by detecting a change in the $SGF_{SFR}$ following exhalation beyond a threshold for example, as compared to when the $O_2$ is closer to a concentration typical in air (e.g., between 20-22% (e.g., approximately 21%)) and/or some other determined standard, threshold, etc. In this way, in accordance with embodiments of the present system, changes in pressure within the sampling chamber that may be caused by the increased gas viscosity of the SGF (e.g., containing 100% $O_2$) beyond a threshold differential pressure value may be utilized to determine that supplemental oxygen is being provided. Accordingly, in a case wherein it is determined that the change of pressure (e.g., DP) is equal to or greater than the threshold pressure value, the process may determine that supplemental oxygen is being provided. However, in a case wherein it is determined that the change of differential pressure (DP) such as across a linear resistor (e.g., flow restrictor) is less than the threshold pressure value, the process may determine that supplemental oxygen is not being provided.

In accordance with embodiments of the present system, the process may for example employ gas sampling methods which may measure a pressure in the sampling chamber and may compensate for example to a measured partial pressure of $CO_2$ back to an equivalent partial pressure at ambient pressure. Accordingly, the process may sense pressure of gas within the sampling chamber in real time and compare this pressure with previous pressures and/or a default pressure(s) such as the ambient pressure to determine whether or not supplemental oxygen is being provided. For example, in a case wherein the differential pressure swing during the breath relative to the sample chamber pressure swing is observed to be larger than 50% for example as caused by the higher viscosity of high $O_2$ concentration in the sample tubing, the present system may determine that supplemental oxygen is being provided and may thereby, provide an indication to that effect.

In accordance with embodiments of the present system, the SGF may, at certain times, include substantially pure exhaled air from the patient as may be readily appreciated. However, when the breath rate of the patient slows (as may occur when administered the above-referenced medications, etc.), supplemental oxygen that is infused into the nostrils of the patient (e.g., supplied via the patient interface), may be drawn into the SGF and analyzed by sensors in accordance with embodiments of the present system. As $O_2$ has a higher viscosity than air, it may cause greater negative pressure when it is drawn into the sample chamber as compared to when typical ambient air is present in the sampling chamber. In other words, as air is displaced from the sample chamber by $O_2$, the negative pressure due to the higher concentration of $O_2$ being drawn into the sample chamber may increase the pressure within the sampling chamber. For example, when the breath rate of the patient slows, the concentration of $O_2$ drawn into the sample chamber may increase rapidly reaching values of up to 100% oxygen as compared to values when obtained at a faster breathing rate.

Referring back to FIG. 3, $CO_2$, DP and $SGF_{SFR}$ signals over time are shown for a patient being ventilated including with and without supplemental oxygen in accordance with embodiments of the present system. As shown, when $O_2$ is present (as provided by the supplemental oxygen), the deviation in each of the DP and $SGF_{SFR}$ signals during each breath are larger and the deviation in the SGF signal (e.g., $\Delta SGF$) becomes larger relative to the deviation of the sample chamber pressure signal (e.g., $\Delta DP$) during the same period. When supplemental oxygen is provided to the patient, the increase in backpressure may cause the pressure in the sampling chamber to exceed the threshold pressure value (ThreshO2) over the course of a sampling time period (ts). The sampling time period may be set by the system so that a sufficient time may be provided to sample desired inspiration and/or expiration gasses of the patient which may be representative of the patient's respiration data. In accordance with embodiments of the present system, when the $O_2$ level rises during exhalation, a larger differential pressure (e.g., an increasing differential pressure over time) may be sensed, which increase may be utilized for determining whether or not supplemental oxygen is being provided.

Further, in accordance with embodiments of the present system, the process may employ gas sampling methods which may measure transient changes in the measured sample flow over the sampling time period and/or portions of the sampling time period (e.g., such as at a time of exhalation and/or following inhalation) and provide this information to the controller for further processing in accordance with embodiments of the present system. For example, in accordance with embodiments of the present system, the process for example during act 211 may utilize detection of transient changes in the measured sample flow, over the sampling time period and/or portions of the sampling time period (e.g., such as at a time of exhalation and/or following inhalation) to determine that supplemental oxygen is being provided. As appreciated in consideration for transient parameters of the present system in these embodiments, since the controller for example may be aiming to adjust the flow back to a target value such as 50 mL/min, the flow changes may be short in duration before the adjustment to the flow rate.

Accordingly, the process may sense one or more of pressure, concentration (e.g., $CO_2$ concentration) and/or transient changes in the measured sample flow of gas within the sampling chamber in real time and compare this for example to one or more threshold values e.g., during act 211, to determine whether or not supplemental oxygen is being provided. In accordance with embodiments of the present system, the process may utilize more than one indicators (e.g., pressure and concentration) to provide a greater confidence in a determination whether or not supplemental oxygen is being provided.

In any event and regardless of how a determination is made, in a case wherein it is determined that supplemental oxygen is/was detected, the process may continue to act 213. However, in a case wherein it was determined that supplemental oxygen is/was not detected, the process may continue to act 215.

In a case wherein it is determined that supplemental oxygen is/was detected, during act 213, the process may render (e.g., generate and display) a message indicating that supplemental oxygen is/was detected such as: "Supplemental oxygen Detected" or the like. This message may be set by the system and/or user and stored in a memory of the system for later use. Further, in accordance with embodiments of the present system, the process may set one or more flags such as an $O_2$ flag to indicate that supplemental oxygen is/was detected. After completing act 213, the process may continue to act 217.

In a case wherein it is determined that supplemental oxygen is/was not detected, the process during act 215 may generate a message indicating that supplemental oxygen is/was not detected such as: "Supplemental oxygen Not Detected" or the like. This message may be set by the system and/or user and may be stored in a memory of the system for later use. Further, in accordance with embodiments of the present system, the process may set one or more flags such as the $O_2$ flag to indicate that supplemental oxygen is/was not detected. After completing act 215, the process may continue to act 217.

With respect to acts 213 and 215, during these acts the process may generate a clinical message (e.g., which may be referred to as a supplemental oxygen message) indicating the results of the determination during act 211. Accordingly, it is envisioned that in accordance with embodiments of the present system, other messages may be set by the system and/or user and may be stored in a memory for later use. In accordance with embodiments of the present system, the process may form a user interface (UI) with which a user may set, reset, enter and/or select a supplemental oxygen message.

During act 217, the process may render the message formed during acts 213 or 215. Further, during this act, the process may also render detected gas levels (e.g., $CO_2$) as, for example a capnogram in real time. In accordance with embodiments of the present system, the message formed during acts 213 or 215 (e.g., "Supplemental oxygen Detected" or "Supplemental oxygen Not Detected") may be superposed upon the capnogram or may be rendered on a standalone rendering device such as one or more dedicated LEDs.

FIG. 5 illustrates a capnogram which shows a graph 500 including a capnogram 502 and a clinical message formed in accordance with one or more embodiments of the present system. In an illustrative embodiment, it is assumed that the process has determined that supplemental oxygen is recommended and is detected. Accordingly, one or more clinical messages such as message 501 may be rendered to inform a user (e.g., a clinician, etc.) that supplemental oxygen is recommended and/or message 503 may be rendered to inform the user of the results of the process such as supplemental oxygen is/was detected. The process may further indicate when supplemental oxygen is detected as shown by line 505 and the corresponding text. The capnogram 502 is shown as corresponding to graph 300 for the sake of clarity.

In accordance with embodiments of the present system, the process may render results of the determination of act 210 using any suitable rendering device for example providing an interface such as a display, speakers, lamps (e.g., RED light emitting diode (LED)=No Supplemental Oxygen Detected; Green LED=Supplemental Oxygen Detected), highlighting (e.g., red highlighting=no supplemental oxygen detected; green highlighting=supplemental oxygen detected), etc. The system may further flash information rendered to draw attention to the information. For example, the system may flash, display and/or otherwise render a supplemental oxygen recommended request.

Further, in accordance with embodiments of the present system, the process may illuminate one or more indicator lights such as LEDs or the like in accordance with the supplemental oxygen flag set during acts 213 or 215. For example, in a case wherein the supplemental oxygen flag indicates that supplemental oxygen is/was detected, the process may illuminate a green LED. However, in a case wherein the supplemental oxygen flag indicates that supplemental oxygen is/was not detected, the process may illuminate a red LED. The LEDs may be the same LED (e.g., a bicolor LED) or separate LEDs (e.g., red and green LEDs). These one or more indicators, such as indicator lights may be mounted on a body of a side-stream capnometry system in accordance with embodiments of the present system.

Further, the system may transmit results of the determination of whether supplemental oxygen is recommended and/or being administered (e.g., as the clinical message, system flags, etc.) to other devices, algorithms, applications (e.g., a clinical decision support application), etc., using any suitable system interface such as a system bus, a network interface, etc. Accordingly, these other devices, algorithms, applications, etc., may be informed for example of the determination of whether supplemental oxygen is/was detected. In accordance with embodiments of the present system, it is envisioned that the recommendation and/or supplemental oxygen flag may be accessed via a network interface to determine for example whether supplemental oxygen is/was detected. After completing act 217, the process may continue to act 219.

During act 219, the process may update a system history which may for example be stored in a memory of the system to record results of the process. In accordance with embodiments of the present system, the process may thereafter repeat act 207 and subsequent acts as shown. The process may end at any time when an end is requested by the system and/or user such as some time when ventilation of the patient is terminated.

Figure 4:
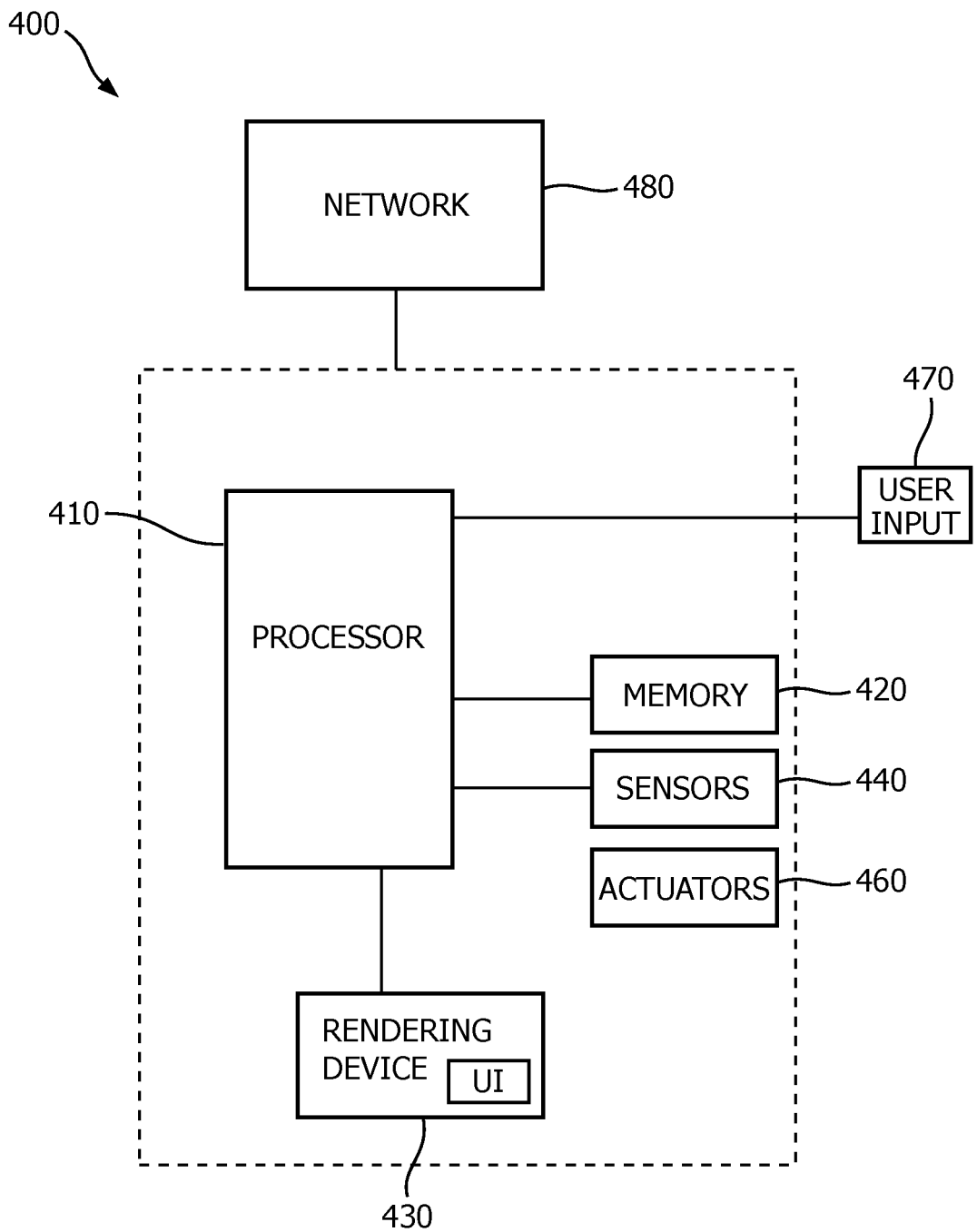
FIG. 4 shows a portion of a system operating in accordance with embodiments of the present system.

FIG. 4 shows a portion of a system 400 in accordance with embodiments of the present system. For example, a portion of the present system may include a processor 410 (e.g., a controller) operationally coupled to a memory 420, a rendering device such as a display 430, sensors 440, actuators 460, a network 480, and a user input device 470. The memory 420 may be any type of device for storing application data as well as other data related to the described operation. The application data and other data are received by the processor 410 for configuring (e.g., programming) the processor 410 to perform operation acts in accordance with the present system. The processor 410 so configured becomes a special purpose machine particularly suited for performing in accordance with embodiments of the present system.

The user input 470 may include a keyboard, a mouse, a trackball, or other device, such as a touch-sensitive display, which may be stand alone or be a part of a system, such as part of a personal computer, a personal digital assistant (PDA), a mobile phone (e.g., a smart phone), a monitor, a wearable display (e.g., smart glasses, etc.), a smart- or dumb-terminal or other device for communicating with the processor 410 via any operable link. The user input device 470 may be operable for interacting with the processor 410 including enabling interaction within a user interface (UI) as described herein. Clearly the processor 410, the memory 420, display 430, and/or user input device 470 may all or partly be a portion of a computer system or other device such as a network coupled device.

The actuators 460 may include one or more motors, transducers, etc., which may provide a force to operate one or more valves, mixers, pump, or the like of the SSM 160 under the control of the processor 410. These actuators may, for example, include pneumatic control valves which may control the flow of one or more gasses for ventilation, may include a pump which may be utilized to draw in the sample as described, etc.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 420 or other memory coupled to the processor 410.

The program and/or program portions contained in the memory 420 may configure the processor 410 to implement the methods, operational acts, and functions disclosed herein. The memories may be distributed, for example accessible over a network connection, or local, and the processor 410, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 410. The memory 420 may include a non-transitory memory. With this definition, information accessible through a network such as the network 480 is still within the memory, for instance, because the processor 410 may retrieve the information from the network 480 for operation in accordance with the present system.

The processor 410 is operable for providing control signals and/or performing operations in response to input signals from the user input device 470 as well as in response to other devices of a network and executing instructions stored in the memory 420. The processor 410 may include one or more of a microprocessor, an application-specific or general-use integrated circuit(s), a logic device, etc. Further, the processor 410 may be a dedicated processor for performing in accordance with embodiments of the present system or may be a general-purpose processor wherein only one of many functions operates for performing in accordance with the present system. The processor 410 may operate utilizing a program portion, multiple program segments, or may be a hardware device utilizing a dedicated or multi-purpose integrated circuit.

Accordingly, embodiments of the present system may provide a gas monitoring system such as a side-stream $CO_2$ monitoring system which may determine whether supplemental oxygen is being administered. During use, a clinician may couple a sampling system interface such as a nasal cannula to a patient. Then, after a period of monitoring the patient's respiration data, a system such as a sidestream SGF monitoring system operating in accordance with embodiments of the present system may monitor a side-stream gas flow and generate and/or render an informational clinical message such as: "Supplemental oxygen Likely Present", "Supplemental oxygen Not Detected", messages of the like and/or others. One or more messages may then be rendered on a rendering device of the system such as a display, a speaker, a lamp, etc. which may be located locally and/or remotely from the system.

Further, the one or more messages may be available locally within the system (e.g., as a parameter, etc.) for the user of other applications of the system such that support the capnogram or otherwise such as clinical decision support (CDS) applications or the like (hereinafter CDS algorithms for the sake of clarity). For example, the addition of supplemental oxygen may distort a measured capnogram. This distortion may make it difficult or impossible to algorithmically identify various conditions of one or more gases within the SGF (e.g., conditions of temperature, volume, concentration, and/or pressure) and/or one or more patient conditions using conventional methods. However, knowledge of the presence or absence of supplemental oxygen in the gas analyzed by the side-stream capnometer operating in accordance with embodiments of the present system may be provided to the algorithms and/or applications which may process this information for example to increase accuracy when supplemental oxygen is used. In accordance with embodiments of the present system, this may not only improve the accuracy of algorithms and/or applications, but may also reduce the number of false alarms for example by correcting the algorithms, correcting the applications and/or by providing an indication of whether supplemental oxygen is being provided.

Further, it is envisioned that embodiments of the present system may analyze a side-stream flow to determine whether supplemental oxygen is being provided and/or provide an alert in a case wherein it determined that a delivery of oxygen may be desirable. Accordingly, a clinician may be provided with an indication such as an alert as a reminder to provide supplemental oxygen when it may be determined that supplemental oxygen may be beneficial to the user as may be determined for example by a CDS algorithm run by a CDS application of the system. For example, in accordance with embodiments of the present system when a patient's respiration rate is determined to be low (e.g., less than 10 breaths per minute for an average adult) and supplemental oxygen is not identified to be turned on, a clinician may be reminded with a message to turn the oxygen on. In accordance with embodiments of the present system, this indication may prevent a clinician from forgetting to provide supplemental oxygen when it would be beneficial.

In accordance with embodiments of the present system, there is provided a system, such as a side-stream capnometer which may analyze ventilation gas and detect the presence of supplemental oxygen in the ventilation gas. The results of this analysis may then be provided as an input to algorithms operative in accordance with embodiments of the present system which may then use this input to identify/monitor patient vitals. These patient vitals may then be analyzed by the system to determine whether to render an alert as described above. In accordance with embodiments of the present system, this may improve accuracy of the above-referenced algorithms and may reduce or entirely prevent false alerts such as providing an alert when an alert condition does not exist.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention. For example, while the above examples of embodiments in accordance with the present system is described with regard to a side stream gas monitoring system, in accordance with further embodiments of the present system, a mainstream monitoring system may be suitably utilized.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow.

Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

The invention claimed is:

1. A capnography system, comprising:
   a controller configured to
      obtain a sample gas flow from a physical interface for a patient;
      determine a change in pressure of the sample gas flow during a sampling time interval using a ratio of a change in sample pressure ($\Delta$SGF) to a change in differential pressure ($\Delta$DP);
      determine whether the change in the pressure of the sample gas flow during the sampling time interval is equal to or greater than a corresponding threshold value;
      determine that supplemental oxygen is provided when it is determined that the change in the pressure of the sample gas flow is equal to or greater than the threshold value;
      determine that the supplemental oxygen is not provided when it is determined that the change in the pressure of the sample gas flow is less than the threshold value; and
      form a message which indicates whether the supplemental oxygen is determined to be provided; and
   a rendering device configured to display the formed message.

2. The capnography system of claim 1, wherein the controller is further configured to
   form a first message which indicates that the supplemental oxygen is recommended when it is determined that the supplemental oxygen is not provided and one or more patient conditions indicates that the supplemental oxygen is recommended, and
   form a second message which indicates that the supplemental oxygen is not recommended when it is determined that the supplemental oxygen is provided and the one or more patient conditions indicates that the supplemental oxygen is not recommended.

3. The capnography system of claim 2, wherein the controller is further configured to
   render a third message that is an alarm message when the controller renders at least one of the first and second messages.

4. The capnography system of claim 1, further comprising:
   a flow restrictor fluidically coupled to the physical interface, wherein the controller is further configured to obtain the sample gas flow through the flow restrictor and determine a change in differential pressure in the sample gas flow.

5. The capnography system of claim 1, wherein the controller is further configured to
   render at least one of concentration and partial pressure of carbon dioxide gas.

6. A capnography system, comprising:
   a controller which:
      obtains a sample gas flow from a physical interface coupled to a user;
      determines a change in pressure of the sample gas flow during a sampling time interval using a ratio of a change in sample pressure ($\Delta$SGF) to a change in differential pressure ($\Delta$DP);
      determines whether the change in the pressure of the sample gas flow during the sampling time interval is equal to or greater than a corresponding threshold value;
      renders results of the determination, wherein the controller is further configured to determine that supplemental oxygen is not provided when it is determined that the change in the pressure of the sample gas flow is less than the threshold value,
      forms a message which indicates whether the supplemental oxygen is determined to be provided, wherein a rendering device is configured to display the formed message.

7. The capnography system of claim 6, further comprising:
   a pneumatic system that provides a ventilation gas to the physical interface for inhalation by the user.

8. The capnograph system of claim 6, wherein the rendering device is further configured to display a graph of the pressure of the sample gas flow during the sampling time interval.

9. A method of determining whether supplemental oxygen is being provided in a capnographic system, the method comprising:
   obtaining, with a controller in the capnographic system, a sample gas flow from a physical interface for a patient;
   determining, with a controller in the capnographic system, a change in pressure of the sample gas flow during a sampling time interval using a ratio of a change in sample pressure ($\Delta$SGF) to a change in differential pressure ($\Delta$DP);
   determining, with the controller in the capnographic system, whether the change to the pressure of the sample gas flow during the sampling time interval is equal to or greater than a threshold value;
   determining, with the controller in the capnographic system, that supplemental oxygen is provided when it is determined that the change in the pressure of the sample gas flow is equal to or greater than the threshold value;

determining, with the controller in the capnographic system, that the supplemental oxygen is not provided when it is determined that the change in the pressure of the sample gas flow is less than the threshold value; and forming a message which indicates whether the supplemental oxygen is determined to be provided.

10. The method of claim 9, further comprising acts of:

determining whether one or more patient conditions indicates that the supplemental oxygen is recommended;

forming a first message which indicates that the supplemental oxygen is recommended when it is determined that the supplemental oxygen is not provided and the one or more patient conditions indicates that the supplemental oxygen is recommended; and forming a second message which indicates that the supplemental oxygen is not recommended when it is determined that the supplemental oxygen is provided and the one or more patient conditions indicates that the supplemental oxygen is not recommended.

11. The method of claim 10, further comprising:

rendering a third message that is an alarm message when the controller renders at least one of the first and second messages.

12. The method of claim 9, further comprising:

determining a change in differential pressure in the sample gas flow.

\* \* \* \* \*